(12) United States Patent
Xiang et al.

(10) Patent No.: US 7,109,706 B2
(45) Date of Patent: Sep. 19, 2006

(54) INTEGRATED EWP-STM SPIN RESONANCE MICROSCOPE

(75) Inventors: Xiao-Dong Xiang, Danville, CA (US); Haitao Yang, San Jose, CA (US)

(73) Assignee: Intematix Corporation, Fremont, CA (US)

( * ) Notice: Subject to any disclaimer, the term of this patent is extended or adjusted under 35 U.S.C. 154(b) by 0 days.

(21) Appl. No.: 11/216,931

(22) Filed: Aug. 30, 2005

(65) Prior Publication Data

US 2006/0071662 A1 Apr. 6, 2006

Related U.S. Application Data

(60) Provisional application No. 60/606,324, filed on Aug. 31, 2004.

(51) Int. Cl.
*G01V 3/00* (2006.01)
(52) U.S. Cl. .................. 324/300; 324/304; 324/316
(58) Field of Classification Search .............. 324/300, 324/304, 316
See application file for complete search history.

(56) References Cited

U.S. PATENT DOCUMENTS

| | | | | |
|---|---|---|---|---|
| 5,489,774 A | * | 2/1996 | Akamine et al. | 250/234 |
| 5,585,722 A | * | 12/1996 | Hosoki et al. | 324/318 |
| 5,619,139 A | * | 4/1997 | Holczer et al. | 324/318 |
| 6,211,532 B1 | * | 4/2001 | Yagi | 257/40 |
| 6,946,835 B1 | * | 9/2005 | Xiang et al. | 324/300 |

* cited by examiner

*Primary Examiner*—Louis M. Arana
(74) *Attorney, Agent, or Firm*—Buchanan, Ingersoll & Rooney

(57) ABSTRACT

A novel spin resonance microscope is disclosed, the microscope design comprising an integrated evanescent wave probe and scanning tunneling microscope tip. The probe and tip may be either the same structure, or they may be separate structures. The integrated design allows for coherent excitation of precessing electron spin states in the sample such that spin resonance may be detected because the tunneling current is modulated by the spin resonance. Spin resonance may be affected by either adjacent nuclei, or by adjacent electrons. The present apparatus requires significantly reduced power inputs, such that the dead time of the system is short, and relaxation phenomena may be evaluated without swamping the instrument's electronics.

42 Claims, 2 Drawing Sheets

INTEGRATED EWP-STM SPIN RESONANCE MICROSCOPE

CROSS-REFERENCE TO RELATED APPLICATIONS

This application claims priority to U.S. Provisional Application No. 60/606,324, filed Aug. 31, 2004, titled "An Integrated EWP-STM Spin Resonance Microscope." U.S. Provisional Application No. 60/606,324 is hereby incorporated by reference in its entirety.

BACKGROUND OF THE INVENTION

1. Field of the Invention

Embodiments of the present invention are directed in general to the field of high-resolution, high-sensitivity nuclear and/or electron spin resonance detection. More specifically, the present invention is directed to evanescent wave probe (EWP) techniques used in conjunction with scanning tunneling microscopy (STM) to detect nuclear and/or electron spin resonance.

2. State of the Art

In the discussion of the state of the art that follows, reference is made to certain structures and/or methods. However, the following references should not be construed as an admission that these structures and/or methods constitute prior art. Applicants expressly reserve the right to demonstrate that such structures and/or methods do not qualify as prior art against the present invention.

Spectroscopy and imaging technologies based on magnetic resonance, e.g., electron spin resonance (ESR), also known as electron paramagnetic resonance (EPR), and nuclear magnetic resonance (NMR) have in the past played critical roles in characterizing fundamental properties of molecular structure and materials as well as playing critical roles in medical diagnosis. Dramatic advances in nanotechnology, quantum computing, proteomics, combinatorial screening of catalysts and the monitoring of other chemical reactions involving free radicals, and biomedical sciences such as drug screening, have increased the sensitivity requirements for nanoscale spatially resolved magnetic resonance spectroscopy and imaging technologies.

Spin label EPR and NMR spectroscopy is a very powerful tool for determining three dimensional (3-D) protein structures/functionality and protein-ligand interaction in drug-screening. Relative to X-ray structural determination, EPR and NMR do not require protein crystal growth, which requirement is a major disadvantage of the x-ray technique, and thus one may study proteins under physiological conditions using EPR and/or NMR. Electron paramagnetic resonance (EPR) spectroscopy of a site-directed spin label (SDSL) on proteins can reveal protein motion and determine protein structure of any size. Compared to fluorescence spectroscopy techniques, in which fluorescent tags are attached to proteins, spin labels are much smaller and less likely to interfere with the protein's native structure and movement. Spin label-EPR techniques are more sensitive and require less protein than NMR, but current instrumentation is much less sensitive than fluorescence spectroscopy. In addition, commercial instrumentation currently available lags behind NMR by about 20 years in that a time resolved pulse measurement capability is not available (due to some fundamental difficulties in instrumentation development). This has slowed and hampered the adaptation of the new SDSL technology in bio-technology.

A typical magnetic resonance (NMR or ESR) system applies radiation in either the RF or microwave region of the electromagnetic spectrum to a sample already subjected to an external magnetic field, wherein the applied radiation may be either continuous or pulsed, and the radiation having a frequency that is tuned to the specific nuclear or electron spin resonance under consideration. The protons (in the case of NMR) or the electrons (in the case of ESR) absorb the energy and precess coherently at a particular frequency in a particular direction. The resonance frequency v of a spin is proportional to the external magnetic field B, and the energy of absorption $hv=g\mu B$, where h is Planck's constant, g is Landé g factor, and $\mu$ is either the nuclear magneton $\mu_N$ for the NMR case, or the Bohr magneton $\mu_B$ for the case of ESR.

In a typical nuclear spin resonance experiment, electronic shielding of nuclear spins will induce a very small so-called "chemical shift" to the nuclear spin resonance. It is possible to measure this small shift when the sample has been placed in a highly uniform magnetic field $B_0$, since the nuclear spin resonance line width is extremely narrow. One of the most powerful features and capabilities of conventional NMR is the structural determination that is possible through precise measurement of the chemical shift. Any non-uniformity in the static magnetic field will tend to smear out the small chemical shift and render a NMR instrument useless for structure determination. In this situation, NMR machines have only the capability of structural determination with large volumes of homogenous specimens, and cannot provide significant spatial resolution.

In contrast, magnetic resonance imaging (MRI) does have the capability of imaging with a certain spatial resolution, which is usually in the mm range. This capability is realized through a high magnetic field gradient generated in the specimen such that the spatial resolution is proportional to the degree of the gradient. Three-dimensional MRI imaging is achieved typically by applying a linear magnetic field gradient during the period that the RF pulse is applied. The field gradient determines a sensitive slice in which the resonance condition, a local function of the applied field, is met. This gradient magnetic field is turned on and off very rapidly, altering the main magnetic field on a very local level. When the RF pulse is turned off, the precessing hydrogen protons slowly decay back to their thermal equilibrium states. An induced transient induction signal in a magnetic resonance experiment is detected using a pickup coil, and the signal is sent to a computer system for processing.

In the magnetic resonance imaging technique the presence of a field gradient smears out chemical shifts and the different resonance peaks (similar nuclear spin resonances having different chemical shifts) become one broad peak. The MRI resonance peak is at least 100 times broader than normal NMR peak. Consequently, conventional MRI imaging techniques lacks the capability of spectroscopy and structural determination. Furthermore, chemical shifts in nuclear spin resonance also limit the spatial resolution of MRI, since a 10 ppm typical chemical shift determines the MRI spatial resolution to an order of millimeters.

In the past, magnetic resonance experiments have been conducted in conjunction with scanning tunneling microscopy (STM), the latter being a revolutionary technique that is capable of atomic resolution. In recent years, ESR-STM has been reported to be able to detect the local precessing of spins on the surface of a semiconducting or conducting material, enabled by observing the microwave modulation of the tunneling current induced by precessing spins when an external magnetic field is applied. This phenomenon has been interpreted as a consequence of the spin-orbital coupling at a single atomic site, where the electron populates a mixed state of two electron spin states (Zeeman levels) split by the applied magnetic field. However, current magnetic resonance-STM experiments rely on the production of spin precessing by random thermal fluctuations. Furthermore, the reported data from these experiments has not been widely reproduced and accepted due to limited sensitivity, and difficulties in impedance matching between the RF portions of the experimental configuration (typically 50 ohms) and the high impedance tunneling current circuits.

What is needed is a method of inducing spin precession and excitation between spin states that does not rely on random thermal fluctuations, such that nuclear and/or spin resonance techniques may be carried out with increased resolution and sensitivity.

SUMMARY OF THE INVENTION

Embodiments of the present invention describe a nondestructive imaging system based on a localized detection of spin resonance spectroscopy. This technology integrates several aspects of magnetic resonance technology with a novel RF and/or microwave evanescent wave detection device (an evanescent wave probe, or EWP), and further includes elements of scanning tunneling microscopy technology. Alternative embodiments combine EWP with a novel optical pumping and background cancellation scheme. The present embodiments will allow sub-micron, nanometer, and ultimately, atomic resolution spin resonance spectroscopy and imaging of inorganic, organic and biological specimens. Technology area wherein the novel integrated EWP-STM spin resonance microscope may be used include nano-technology, quantum computing, proteomics, combinatorial screening of catalysts, the monitoring of chemical reactions involving free radicals, biomedical sciences, and drug screening.

In one embodiment of the present invention, the integrated EWP-STM spin resonance microscope comprises a microwave/RF resonator cavity coupled to an input power source and an output signal circuit (where the input power source may deliver either radio frequency or microwave energy to the resonator cavity); an evanescent wave probe (EWP) connected to one end of the resonator cavity, the probe configured to coherently excite a precessing electron spin state in an adjacent sample, the precessing electron spin state having a spin resonance frequency; and a scanning tunneling microscope (STM) comprising a bias voltage circuit connected to the resonator cavity and the sample such that the EWP functions also as the tip of the STM. The tunneling current from the STM circuit is modulated by the spin resonance frequency, thereby enabling the detection of a spin resonance in the sample.

In an alternative embodiment of the integrated EWP-STM spin resonance microscope, the microscope comprises a microwave/RF resonator cavity coupled to an input power source and an output signal circuit, and the evanescent wave probe (EWP) comprises a loop structure wherein one end of the loop is connected to a central conductor of the resonator cavity and the other end of the loop is connected to a wall of the resonator cavity. The probe is configured to coherently excite a precessing electron spin state in an adjacent sample, where the precessing electron spin state has a spin resonance frequency. As before, this embodiment of the spin resonance microscope includes a scanning tunneling microscope (STM) comprising a bias voltage circuit connected to a tip of the STM and to the sample. The STM tip extends through the central conductor of the resonator and protrudes through the loop of the evanescent microwave probe. Again, the tunneling current from the STM circuit is modulated by the spin resonance frequency, thereby enabling the detection of a spin resonance in the sample.

In alternative embodiments, the EWP probe and the STM tip may constitute separate structures, but the overall advantages offered by such an instrument, and operating concepts, remain the same.

Spin echo and optical pumping techniques may be used with the present EWP-STM embodiments to even further enhance the sensitivity and resolution characteristics of the spin resonance signal in question.

DETAILED DESCRIPTION OF THE INVENTION

Figure 1:
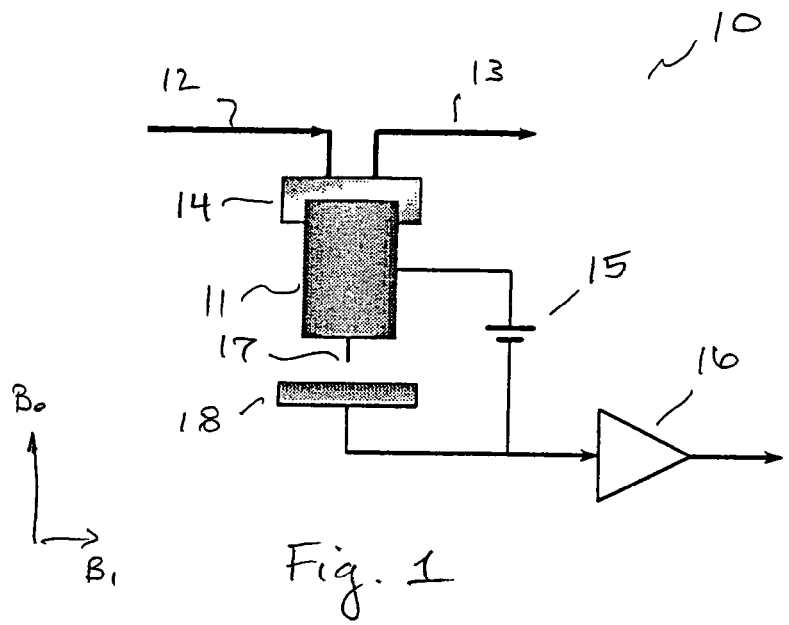
FIG. 1 is a schematic illustration of an integrated EWP-STM instrument design at the level of the resonator, sample, and tunneling current circuit.

Embodiments of the present invention are directed to the field of high-resolution, high-sensitivity nuclear spin resonance and/or electron spin resonance detection by utilizing evanescent wave probe (EWP) techniques in conjunction with scanning tunneling microscopy. In the following disclosure, evanescent wave probe techniques will be discussed along with scanning tunneling microscopy (STM), and techniques by which the two may be integrated. Included in the discussion will be pulsed electron resonance spin (ESR) techniques that may be used with the integrated EWP-STM probe, as well as optical pumping techniques that may be used to excite the precessing spin state.

Embodiments of the presently integrated EWP-STM design emphasize the ability of the EWP probe to excite, pick up and enhance a spin resonance signal from sample. Advantages of the current design include an unprecedented flexibility in setting experimental parameters such that the desired resonance signal may be detected. For example, to distinguish the modulated tunneling current from the EWP sensed signal (where "EWP sensed signal" means the signal detected directly by the EWP probe, rather than through the tunneling current), the tip-sample distance or tunneling bias voltage may be changed and/or modulated, and thus the ESR signal may be detected according to the tip-sample distance or bias voltage change. That portion of the ESR signal which is related to the bias voltage change is ideally contributed by the tunneling current component, and the other portion is the EWP inductively sensed signal directly from the sample rather than through the tunneling current. This technique provides a unique capability for conducting electron spin resonance spectroscopy on a single atom or molecule of a sample.

Integrated EWP and STM Tip Structures

The evanescent microwave probe is a highly sensitive spin resonance detection technique that operates by sending microwaves generated by a microwave resonator to a conducting tip that is part of the evanescent microwave probe; the probe then sends the evanescent microwaves into a sample. The interaction that results is detected by the same EWP tip. Evanescent waves are generated by the EWP tip because the tip radius is much smaller than the wavelength of the microwaves in question. This interaction between the sample and the evanescent microwaves delivered from the EWP tip depend on the complex electrical-magnetic impedance of the sample. The interaction depends on both the real and the imaginary parts of the impedance, and thus there are changes in resonant frequency ($f_r$) and quality factor (Q) of the resonator as a result of that interaction. Advantages of the present embodiments are that the EWP can simultaneously measure both the real and imaginary parts of the sample's electrical impedance, as well as the surface topography, by detecting the shift in resonance frequency and quality factor of the resonator as a result of the interaction. It will be understood by those skilled in the art that evanescent waves, also known as near-field waves, differ from far-field waves in that evanescent waves do not radiate or propagate in space, but rather are localized to (and only present near) the surface of the sharp, conducting, EWP tip. Evanescent (near-field) waves have a much higher spatial resolution than propagating (far-field) waves, and the enhanced resolution is on the order of the wavelength ($\lambda$) of the wave. The evanescent waves of the present embodiments may have energy in either the RF or microwave region(s) of the spectrum.

To achieve even better spatial resolution, meaning down to the atomic level, and to achieve an enhanced sensitivity that can detect a single spin resonance, the present embodiments implement an approach based on the detection of electron and/or nuclear spin resonance via a tunneling current used in conjunction with the inventors' EWP technology. In this approach, the tip of the evanescent wave probe (EWP) also serves as the tip of a scanning tunneling microscope (STM), and thus it is possible to simultaneously perform electron-tunneling measurements with the measurements previously disclosed for the EWP.

An integrated EWP-STM system is shown generally at 10 in FIG. 1. Referring to FIG. 1, a microwave resonator probe comprises a resonator cavity 11, which is electrically isolated from the microwave (or RF) input 12 and output 13 through a coupling kit 14, such that a bias voltage 15 and current amplifier 16 may be connected to the EWP/STM tip 17 to enable the STM mode. The microwave signal is coupled into or out of the resonator 11 via the isolated coupling kit 14. The sample is located at reference numeral 18 in FIG. 1, and it is shown immersed in a static magnetic field $B_0$, where it is usually desired to have this externally applied magnetic field $B_0$ be as uniform as possible. Thus, the EWP probe may be operated as an electron spin resonance excitation source and/or passively as a detector. The STM and EWP probe share the same tip, and thus the modulation signal of the tunneling current, which was induced by the spin resonance, will be coupled into the EWP-STM probe.

In one embodiment of the present invention, the input power source and the output signal circuit of the spin resonance microscope are coupled to the resonator through separate ports, such that transmitted power is measured by the microscope. In an alternative embodiment of the present invention, the input power source and the output signal circuit of the spin resonance microscope are coupled to the resonator through the same port, such that reflected power is measured by the microscope. These two embodiments are not specifically illustrated in FIG. 1; rather, the figure simply shows that a coupling kit 14 may be arranged to serve a variety of desired configurations.

The present design illustrated in FIG. 1 dramatically increases the detection sensitivity since the resonator provides a substantially ideal impedance match between the tunneling and microwave circuits. An additional advantage is that the signal derived from the microwave modulation of the tunneling current will be resonantly enhanced by about a factor of Q (i.e., from about 10 to 1,000) before being amplified by the low noise microwave amplifier.

Separated STM and EWP Tip Structures

Figure 2:
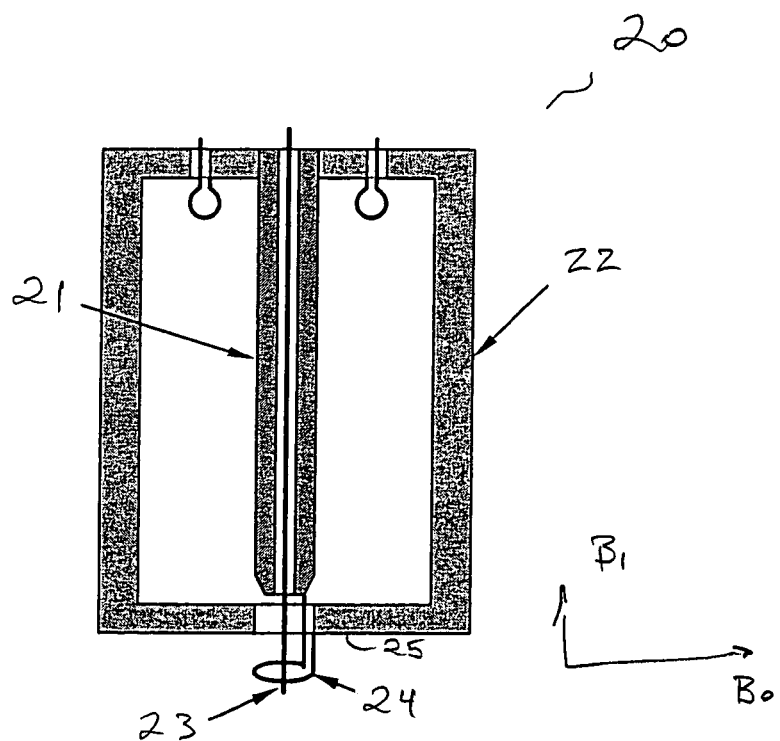
FIG. 2 shows an exemplary EWP-STM probe tip, in this case where the STM tip and an EWP loop are separate structures.

An alternative embodiment is illustrated in FIG. 2, where the probe tip of an exemplary integrated EWP-STM system has separate STM tip and EWP loop structures. Referring to FIG. 2, the microwave or RF generator shown generally at 20 comprises an EWP center conductor 21 within EWP resonator cavity 22, STM tip 23, and EWP loop 24. In this case, the EWP tip of previous embodiments is replaced by loop structure 24. The conductive loop 24 is electrically connected to the EWP cavity center conductor 21, and the outside shielding wall 25, and lies in the horizontal plane perpendicular to the center axis of the cavity 22. The STM tip 23 extends throughout the length of the EWP cavity 22, and is inside and coaxial with the center conductor 21, but is in electrical isolation to the EWP probe 20. Additionally, the STM tip 23 extends through the center of the loop 24.

Advantages of the EWP-STM structure depicted in FIG. 2 are that the small EWP loop 24 is contemplated to produce a magnetic field several orders of magnitude higher than the magnetic fields produced by other configurations. This can be especially advantageous for sensitivity enhancement or in critical applications requiring a condition of strong magnetic field. In the following discussion an intrinsic spin resonance sensitivity analysis is provided based on EWP direct spin resonance detection with a loop structure using a pulse technique; however, the same principles apply to the present EWP-STM structures with regard to the relationships between sensitivity, loop dimensions, and noise analysis.

In one embodiment of the present microscope, the diameter of the EWP loop ranges from about 1 micron to about 1 mm. In an alternative embodiment, the diameter of the EWP loop ranges from about 10 to about 100 microns.

As discussed by D. I. Hoult and N. S. Ginsberg in an article titled, "The quantum origins of the free induction decay signal and spin noise," Journal of Magnetic Resonance, 148, pp. 182–199 (2001) the electrical field generated by a small sample with a time varying magnetic moment $\vec{M}$ is given by (in SI units):

$$\vec{E} = \left(\frac{\mu_0}{4\pi r^3}\right)\vec{r} \times \left(\vec{\dot{M}} + \frac{r}{c}\vec{\ddot{M}}\right) \qquad (1)$$

Assuming the receiving coil has radius $r_0$ with coil plane normal direction in the x-y plane, the external magnetic field $\vec{B}_0$ is along z axis, and the sample located in the coil center has negligible spatial extent (most applicable for intrinsic sensitivity analysis since only a very small number of spins are involved here) with spin moment $\vec{M}$ rotating inside x-y plane at Larmor frequency $\omega_0$, the electric field generated along receiving coil is:

$$E = \frac{\mu_0 \omega_0 M_0}{4\pi r_0^2}\left(1 + i\frac{r_0 \omega_0}{c}\right)e^{i\omega_0 t} \qquad (2)$$

The first term of equation (2) is the effect of near field Faraday induction, and second term is the radiation term (which can propagate to the far field). It will be apparent to one skilled in the art that, in a low frequency range and with a small pick up coil radius (a condition applicable to substantially all NMR spectroscopy instruments), a near field induction effect dominates, while in a high frequency range and with large receiving loop radius situations, the radiation term (applicable to most MRI and ESR high frequency instruments), is proportional to $r_0 \omega_0/c = 2\pi r_0/\lambda$, and this term may dominate the effect. Careful evaluation of these two different mechanisms and attention paid to the consequences of a frequency and radius dependence, have not to the inventors' knowledge been practiced in any previous sensitivity analysis.

In the case of the present evanescent wave spin resonance probe, an evanescent wave condition ($2\pi r_0/\lambda \leq 1$) is always satisfied, so that radiation term is always smaller than near field induction term. The maximum signal power (the induction term) the receiving coil with n turns could generate as a signal output is given by:

$$P_S = \frac{n^2}{32} \frac{\mu_0^2 \omega_0^2 M_0^2}{r_0^2} \frac{1}{R_C} \qquad (3)$$

where $R_C$ is the coil's RF resistance, and $$R_C = n\frac{2\pi r_0}{d}\sqrt{\frac{\mu_0 \omega_0}{2\sigma}}$$

with coil cross dimension d and conductivity $\sigma$. The magnetic moment $M_0$ of sample volume $V_S$ is given by:

$$M_0 = V_S \chi_0 B_0 / \mu_0 \qquad (4)$$
$$= N g \mu_B J(J+1)\frac{\hbar \omega_0}{3kT}$$

where $\mu_B$ is the Bohr magneton for electron spin.

The intrinsic minimum detectable spin number is limited by coil output Johnson noise:

$$N_{min} = \frac{24\sqrt{\pi}}{\hbar \mu_0^{3/4} g\mu_B J(J+1)(2\sigma)^{1/4}\sqrt{Nd}} r_0^{3/2} \omega_0^{-7/4}(kT)^{3/2}(\Delta B)^{1/2} \qquad (5)$$

This parameter is proportional to $r_0^{3/2}\omega_0^{-7/4}(\Delta B)^{1/2}$. To increase the sensitivity, embodiments of the present invention advantageously select a high excitation frequency, low detection bandwidth, and most importantly, a small loop radius. This relation clearly points out the important consequence of having a small curvature evanescent probe as the detection probe for spin resonance.

Furthermore, the above formula teaches the effect of a spin population difference at a given temperature. Since in some embodiments of the present invention it is possible to overcome this problem; i.e. by having fully polarized spins even at room temperature, the above formula may be written without including this factor:

$$N_{min} \approx \frac{8\sqrt{\pi}}{\mu_0^{3/4} g\mu_B J(J+1)(2\sigma)^{1/4}\sqrt{Nd}} r_0^{3/2} \omega_0^{-3/4}(kT\Delta B)^{1/2} \qquad (6)$$

An exemplary embodiment provides for a single turn copper loop with a radius of 10 μm and a cross dimension of 2 μm, such that with a 9.4 GHz excitation frequency and a 4.2 K temperature, an intrinsic ESR sensitivity of $3.7 \times 10^2$ spin/$\sqrt{Hz}$ may be realized.

In the EWP-STM structure depicted in FIG. 2, the microwave frequency modulation of the STM tunneling current (which is DC) is coupled to the EWP loop 24, and therefore spin resonance information may be conveyed to the EWP probe 24 via the tunneling modulation signal.

Pulsed ESR Techniques

One of the most important advances in NMR spectroscopy occurred roughly two decades ago with the development of pulsed (time resolved) Fourier transformation (FT) instrumentation. There are several key advantages offered by the pulsed Fourier transform technique. First, the sensitivity of an instrument can be potentially vastly improved relative to continuous wave (CW) techniques. Second, the pulsed Fourier transform technique is capable of performing spin echo and other higher dimensional quantum correlation experiments.

The ability to perform spin echo experiments with a scanning tunneling microscope setup is significant. Previously reported ESR-STM experiments relied upon random thermal fluctuations (or even unknown, or unclear mechanisms) to generate the mixed Zeeman states necessary for the observation of a modulated tunneling current. Only a very few materials systems have been reported to show such phenomena, and then only under very special conditions. According to embodiments of the present invention, pulsed ESR techniques in conventional spin echo or two-dimensional Fourier transform electron spin resonance (2D-FT-ESR) spectroscopy may be utilized to excite coherently precessing mixed spin states of electrons to ensure the modulation of a tunneling current by the spin resonance in a sample.

Figure 3:
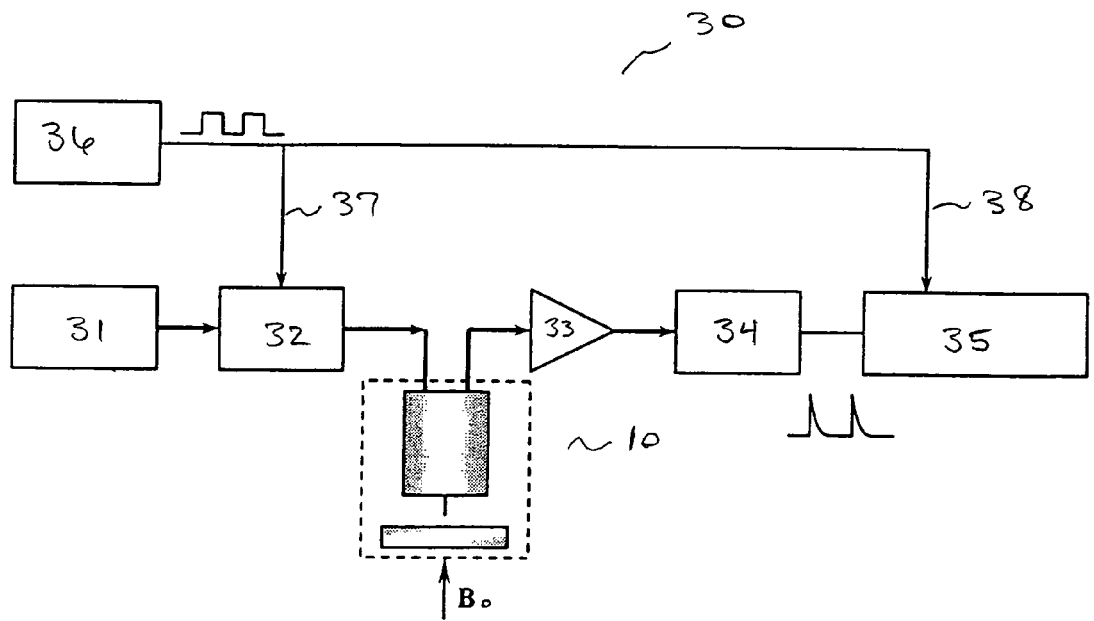
FIG. 3 is a schematic illustration of the present EWP-STM integrated probe with electronics (shown in block format) that may be used to operate the probe in a pulsed configuration for detecting spin resonance.

An exemplary system for carrying out such a pulsed excitation experiment to detect electron spin resonance using the present EWP-STM technique is illustrated in FIG. 3. Referring to FIG. 3, an EWP-STM system configured to conduct pulsed experiments is shown generally at 30. It comprises an integrated EWP-STM probe 10, which has already been discussed in reference to FIG. 1 or FIG. 2, receiving input energy from an RF source 31 via a switch 32. The output signal from probe 10 is first passed to a low noise amplifier 33, whereupon the amplified signal is sent to detector 34 and data acquisition system 35. Pulsing of the RF input signal is provided by pulse generator 36, which provides a trigger signal 37 to the switch 32, as well as a trigger signal 38 to the data acquisition system 35.

In one method of using the apparatus of the present embodiments, an initial π/2 radio frequency (RF) pulse emitted by the EWP component of the probe creates an initial local electron spin state on the sample surface, where the spins are transverse to the external magnetic field $B_0$. Each electron's spin wave function in such an initial state is actually a coherent superposition of spin-up and spin-down eigenstates, which are split in the magnetic field by the Zeeman energy $\Delta E = g \, \mu_B B$. Coherent evolution under the spin Hamiltonian results in an oscillation between the two eigenstates. Classically, this oscillation corresponds to the precession of the spin vector at the Larmor frequency $\Delta E/h$ in a plane normal to the applied magnetic field. This kind of spin oscillation (or precession) will therefore introduce a modulation of the tunneling current in a frequency equal to Larmor frequency.

In an alternative embodiment, a series of RF pulses may be delivered to the sample after the initial excitation pulse.

EWP-STM and the Spin Echo Technique

In the present embodiments, the spin echo technique is used to overcome the quantum de-coherence of spins that can occur as a result of the randomization of spin directions; a phenomenon known as spin-spin relaxation, and characterized by the transverse relaxation time $T_2$. A "spin echo" is created when a transverse magnetization is created in the sample by applying a 90° radiofrequency pulse; the transverse magnetization then decays away as a result of a spreading out of frequencies due to inhomogeneities in the applied $B_0$ field; the 90° pulse is then followed by a 180° pulse, which refocuses the transverse magnetization such that it grows back to form an echo. The spin echo technique is useful because it can mitigate the effects of both inhomogeneities in the applied $B_0$ field, and chemical shifts arising from the chemistry of the sample.

Most commercially available ESR spectrometers are still of the conventional continuous wave (CW) design, and only limited academic efforts have been made to adapt pulse techniques to ESR. There are at least two reasons for this. First, most ESR experiments involve relaxation times that are much shorter than those encountered in NMR, and second, it is difficult to reduce the ESR system relaxation time (known in the art as "dead time") to below the sample relaxation time, a necessary condition if meaningful information is to be extracted. Spin echo experiments apply an intense microwave radiation pulse to the sample to rotate electron spins by angles of either π/2 (to create the transverse magnetization), or π (to refocus the transverse magnetization) in a time period that is much shorter than either the spin-lattice relaxation time $T_1$ or the spin-spin relaxation time $T_2$. Input microwave powers on the order of several thousand watts are typically required, which is orders of magnitude larger than the ESR signal. The ESR signal is so small that it can generally be detected only after the intense excitation power has decayed to a level that is within the dynamic range of the detection electronics; this decay time is defined as "dead time." The dead time has to be short enough so that the ESR signal decay due to the spin-lattice and spin-spin relaxation mechanisms (quantified by $T_1$ and $T_2$, respectively) is not so strong as to have completely quenched the ESR signal prior to the expiration of the dead time. State of the art experimental set-ups (in existence at just a few universities) have demonstrated dead times on the order of about 50 to about 150 nanoseconds; as a consequence, only a very limited number of sample systems may be investigated.

The dead time $T_d$ can be calculated using the following equation:

$$T_d = (P_s - P_r)/d_r \quad (7)$$

where $P_s$ is the input excitation signal power in units of dBm, $P_r$ is highest detectable power level (dBm) within detection system's dynamic range, and $d_r$ is the resonator power damping rate (dB/s) given by:

$$d_r = -10 \log\left(\exp\left(-\frac{1}{\tau_r}\right)\right) \quad (8)$$
$$= \frac{4.34}{\tau_r}$$

In equation (8), the resonator time constant $\tau_r = Q_L/f_0$ with quality factor $Q_L$ and resonant frequency $f_0$. From the dead time equation, one skilled in the art will note that dead time is shorter with lower input signal power or lower $Q_L$.

Embodiments of the present EWP-STM design address these deficiencies that have existed in the art to date. Due to the small curvature tip of EWP probe, a $B_1$ field can be provided that is as high as any of those contemplated to be required, and these exceptionally high fields may be generated with an input power 12 to the resonator 11 as low as about 10 to about 100 milliwatts. (In some embodiments, the input power source is configured to deliver power to the resonator with a power ranging from about 1 milliwatt to about 10 watts). In other words, the input resonator power that is required to generate any field necessary is at 4 orders of magnitude less than that the power required in conventional ESR systems. As a consequence, due to the exponential nature of the decay, this present EWP-STM systems realize dead times that are at least 4 times shorter than the dead times demonstrated by state of art ESR set-ups, given the same $B_1$ field, operating frequency, and electronics dynamic range. Furthermore, it is contemplated that with the small excitation signal levels, faster microwave switches and other components may be used to reach an intrinsic limit of the dead time. Even further improvements (reductions in dead time) may be realized by implementing an EWP-STM design comprising a bimodal resonator structure with orthogonal modes.

It is contemplated that a dead time of the detection electronics as low as about 5 to about 10 nanoseconds may be achieved with the improvements offered by the present EWP-STM embodiments. With such an instrument available, it will become feasible to perform pulse spin echo experiments on a much wider range of sample types than is currently available. In alternative embodiments, the dead time of the detection electronics is configured to be about 1 to about 100 nanoseconds, and about 5 to about 20 nanoseconds.

EWP-STM and Optical Pumping

Figure 4:
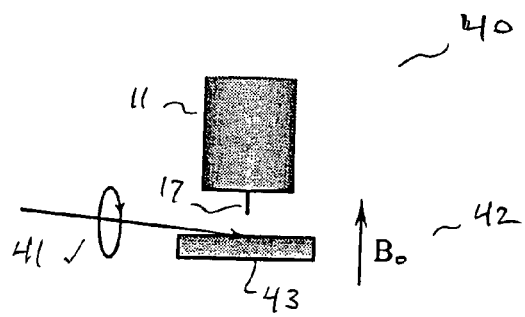
FIG. 4 is a schematic illustration of an optical pumping scheme for detecting electron spin resonance.

Optical pumping is another technique that can be used to excite precessing spin states. As illustrated in FIG. 4, the optically pumped EWP-STM system shown generally at reference numeral 40 comprises a circularly polarized laser pulse 41 aligned perpendicularly to an applied external magnetic field 42. The polarized laser pulse 41 is directed toward a surface of a sample 43. In one embodiment of the present invention, the sample 43 may be a semiconductor.

For the purposes of the present description, it will be assumed that the sample 43 is a semiconductor. According to the present embodiments, the circularly polarized laser pulse 41 creates an initial electronic state in the conduction band of the semiconductor sample 43 in which all the optically excited spins are oriented in a transverse direction relative to the external magnetic field 42. Repetitive laser pulses may be applied to the semiconductor sample 43 to resonantly build spin precession; if this is the case, then it is desirable to set the interval of pulses to a value such that the precession frequency maintains the electron spins in phase for successive pulses. Incoherent evolution of the spin's wave function will usually result in a departure from a smooth oscillatory behavior. Therefore, by increasing the interval of successive pulses, and measuring the change in the amplitude of the tunneling current, a spin decay behavior can be measured and correlated to spin relaxation time. These embodiments are contemplated to be capable of enabling spin resonance detection in a wide range of materials systems. For example, semiconductor materials will most likely be used in quantum computing application, and due to the small population difference between Zeeman states of the participating electrons, optical pumping techniques will be high advantageous in conjunction with the present EWP-STM embodiments to generate an initial precessing spin state for the system.

In one embodiment of the present invention, an integrated EWP-STM spin resonance microscope comprises a microwave/RF resonator cavity coupled to a source for supplying optical pumping to the sample to excite a precessing electron spin state in an adjacent sample. The precessing electron spin state has a resonance frequency. The optical pumping is applied perpendicularly to an externally applied magnetic field, and the microwave/RF resonator cavity is also coupled to an output signal circuit. An evanescent wave probe (EWP) connected to one end of the resonator cavity, where the probe is configured to coherently detect the precessing electron spin state in the adjacent sample. The microscope further comprises a scanning tunneling microscope (STM) with a bias voltage circuit connected to the resonator cavity and to the sample such that the EWP functions also as the tip of the STM.

In this embodiment, the tunneling current from the STM circuit is modulated by the spin resonance frequency, thereby enabling the detection of a spin resonance in the sample. The spin resonance signal may be derived from a spin-orbital coupling effect, or it may be derived from nuclear spin resonance through a hyperfine interaction between a nucleus and an electron in the sample.

Many modifications of the exemplary embodiments of the invention disclosed above will readily occur to those skilled in the art. Accordingly, the invention is to be construed as including all structure and methods that fall within the scope of the appended claims.

What is claimed is:

1. An integrated EWP-STM spin resonance microscope, the microscope comprising:
    a microwave/RF resonator cavity coupled to an input power source and an output signal circuit;
    an evanescent wave probe (EWP) connected to one end of the resonator cavity, the probe configured to coherently excite a precessing electron spin state in an adjacent sample, the precessing electron spin state having a spin resonance frequency; and
    a scanning tunneling microscope (STM) comprising a bias voltage circuit connected to the resonator cavity and to the sample such that the EWP functions also as the tip of the STM;

wherein the tunneling current from the STM circuit is modulated by the spin resonance frequency, thereby enabling the detection of a spin resonance in the sample.

2. The spin resonance microscope of claim 1, wherein the input power source and the output signal circuit are coupled to the resonator through separate ports, such that transmitted power is measured by the microscope.

3. The spin resonance microscope of claim 1, wherein the input power source and the output signal circuit are coupled to the resonator through the same port, such that reflected power is measured by the microscope.

4. The spin resonance microscope of claim 1, wherein the input power source delivering power to the microwave/RF resonator is configured to deliver power ranging from about 1 milliwatt to about 10 watts.

5. The spin resonance microscope of claim 4, wherein the input power source delivering power to the microwave/RF resonator is configured to deliver power ranging from about 10 to about 100 milliwatts.

6. The spin resonance microscope of claim 1, wherein the dead time of the detection electronics is configured to be about 1 to about 100 nanoseconds.

7. The spin resonance microscope of claim 1, wherein the dead time of the detection electronics is configured to be about 5 to about 10 nanoseconds.

8. The spin resonance microscope of claim 1, wherein the dead time of the detection electronics is configured to be about 5 to about 20 nanoseconds.

9. The spin resonance microscope of claim 1, wherein the input power source is configured to deliver continuous wave (CW) power to the resonator cavity.

10. The spin resonance microscope of claim 1, wherein the input power source is configured to deliver pulsed power to the resonator cavity.

11. The spin resonance microscope of claim 10, wherein the input power source is configured to deliver at least one 90° pulse to the sample.

12. The spin resonance microscope of claim 10, wherein the input power source is configured to deliver at least one 180° pulse to the sample.

13. The spin resonance microscope of claim 1, wherein the integration of the EWP and STM portions of the microscope is configured to enhance the signal derived from the modulation of the tunneling current by a quality factor Q ranging from about 10 to about 1,000.

14. The spin resonance microscope of claim 1, wherein the spin resonance signal is derived from a spin-orbital coupling effect.

15. The spin resonance microscope according to claim 1, wherein the spin resonance signal is derived from nuclear spin resonance through a hyperfine interaction between a nucleus and an electron in the sample.

16. An integrated EWP-STM spin resonance microscope, the microscope comprising:
    a microwave/RF resonator cavity coupled to an input power source and an output signal circuit;
    an evanescent wave probe (EWP) comprising a loop structure wherein one end of the loop is connected to a central conductor of the resonator cavity and the other end of the loop is connected to a wall of the resonator cavity, the probe configured to coherently excite a precessing electron spin state in an adjacent sample, the precessing electron spin state having a spin resonance frequency; and
    a scanning tunneling microscope (STM) comprising a bias voltage circuit connected to a tip of the STM and to the sample, the STM tip extending through the central conductor of the resonator and protruding through the loop of the evanescent microwave probe;

wherein the tunneling current from the STM circuit is modulated by the spin resonance frequency, thereby enabling the detection of a spin resonance in the sample.

17. The spin resonance microscope of claim 16, wherein the input power source and the output signal circuit are coupled to the resonator through separate ports, such that transmitted power is measured by the microscope.

18. The spin resonance microscope of claim 16, wherein the input power source and the output signal circuit are coupled to the resonator through the same port, such that reflected power is measured by the microscope.

19. The spin resonance microscope of claim 16, wherein the input power source delivering power to the microwave/RF resonator is configured to deliver power with a range of about 1 milliwatt to about 10 watts.

20. The spin resonance microscope of claim 16, wherein the input power source delivering power to the microwave/RF resonator is configured to deliver power with a range of about 10 to about 100 milliwatts.

21. The spin resonance microscope of claim 16, wherein the dead time of the detection electronics is configured to be about 1 to about 100 nanoseconds.

22. The spin resonance microscope of claim 16, wherein the dead time of the detection electronics is configured to be about 5 to 10 about nanoseconds.

23. The spin resonance microscope of claim 16, wherein the dead time of the detection electronics is configured to be about 5 to 20 about nanoseconds.

24. The spin resonance microscope of claim 16, wherein the input power source is configured to deliver continuous wave (CW) power to the resonator cavity.

25. The spin resonance microscope of claim 16, wherein the input power source is configured to deliver pulsed power to the resonator cavity.

26. The spin resonance microscope of claim 25, wherein the input power source is configured to deliver at least one 90° pulse to the sample.

27. The spin resonance microscope of claim 25, wherein the input power source is configured to deliver at least one 180° pulse to the sample.

28. The spin resonance microscope of claim 16, wherein the integration of the EWP and STM portions of the microscope is configured to enhance the signal derived from the modulation of the tunneling current by a quality factor Q ranging from about 10 to about 1,000.

29. The spin resonance microscope of claim 16, wherein the diameter of the EWP loop ranges from about 1 micron to about 1 mm.

30. The spin resonance microscope of claim 16, wherein the diameter of the EWP loop ranges from about 10 to 100 microns.

31. The spin resonance microscope according to claim 16, wherein the spin resonance signal is derived from a spin-orbital coupling effect.

32. The spin resonance microscope according to claim 16, wherein the spin resonance signal is derived from a nuclear spin resonance through a hyperfine interaction between a nucleus and an electron in the sample.

33. An integrated EWP-STM spin resonance microscope, the microscope comprising:

a microwave/RF resonator cavity coupled to a source for supplying optical pumping to the sample to excite the precessing electron spin state, the optical pumping applied perpendicularly to an externally applied magnetic field;

the microwave/RF resonator cavity further coupled to an output signal circuit;

an evanescent wave probe (EWP) connected to one end of the resonator cavity, the probe configured to coherently detect a precessing electron spin state in an adjacent sample, the precessing electron spin state having a spin resonance frequency; and a scanning tunneling microscope (STM) comprising a bias voltage circuit connected to the resonator cavity and to the sample such that the EWP functions also as the tip of the STM;

wherein the tunneling current from the STM circuit is modulated by the spin resonance frequency, thereby enabling the detection of a spin resonance in the sample.

34. The spin resonance microscope of claim 33, wherein the optical pumping source comprises a circularly polarized laser pulse.

35. The spin resonance microscope according to claim 33, wherein the spin resonance signal is derived from a spin-orbital coupling effect.

36. The spin resonance microscope according to claim 33, wherein the spin resonance signal is derived from nuclear spin resonance through a hyperfine interaction between a nucleus and an electron in the sample.

37. A method of detecting a spin resonance signal in a sample, the method comprising:

providing an integrated EWP-STM spin resonance microscope having a microwave/RF resonator cavity coupled to an input power source and an output signal circuit, and an evanescent wave probe (EWP) connected to one end of the resonator cavity;

further providing a scanning tunneling microscope (STM) comprising a bias voltage circuit connected to the resonator cavity and the sample such that the EWP functions also as the tip of the STM; and coherently exciting a precessing electron spin state in the sample with the probe, the precessing electron spin state having a spin resonance frequency;

wherein the tunneling current from the STM circuit is modulated by the spin resonance frequency, thereby enabling the detection of a spin resonance in the sample.

38. The method of claim 37, wherein the method is used in an application selected from the group consisting of nano-technology, quantum computing, proteomics, combinatorial screening of catalysts, the monitoring of chemical reactions involving free radicals, biomedical sciences, and drug screening.

39. A method of detecting a spin resonance signal in a sample, the method comprising:

providing an integrated EWP-STM spin resonance microscope having a microwave/RF resonator cavity coupled to an input power source and an output signal circuit, and an evanescent wave probe (EWP) connected to one end of the resonator cavity, the EWP comprising a loop structure having one end of the loop connected to a central conductor of the resonator cavity, and the other end of the loop connected to a wall of the resonator cavity;

further providing a scanning tunneling microscope (STM) comprising a bias voltage circuit connected to a tip of the STM and the sample, the STM tip extending through the central conductor of the resonator and protruding through the loop of the evanescent microwave probe; and coherently exciting a precessing electron spin state in the sample with the probe, the precessing electron spin state having a spin resonance frequency;

wherein the tunneling current from the STM circuit is modulated by the spin resonance frequency, thereby enabling the detection of a spin resonance in the sample.

40. The method of claim 39, wherein the method is used in an application selected from the group consisting of nano-technology, quantum computing, proteomics, combinatorial screening of catalysts, the monitoring of chemical reactions involving free radicals, biomedical sciences, and drug screening.

41. A method of detecting a spin resonance signal in a sample, the method comprising:

providing an integrated EWP-STM spin resonance microscope having a microwave/RF resonator cavity coupled to an output signal circuit, and an evanescent wave probe (EWP) connected to one end of the resonator cavity;

further providing a scanning tunneling microscope (STM) comprising a bias voltage circuit connected to a tip of the STM and the sample; and optically pumping energy to the sample to coherently excite a precessing electron spin state in the sample, the precessing electron spin state having a spin resonance frequency;

wherein the tunneling current from the STM circuit is modulated by the spin resonance frequency, thereby enabling the detection of a spin resonance in the sample.

42. The method of claim 41, wherein the method is used in an application selected from the group consisting of nano-technology, quantum computing, proteomics, combinatorial screening of catalysts, the monitoring of chemical reactions involving free radicals, biomedical sciences, and drug screening.

* * * * *